(12) United States Patent
Dorn et al.

(10) Patent No.: US 7,046,893 B2
(45) Date of Patent: May 16, 2006

(54) LAYER STRUCTURE AND OPTICAL WAVEGUIDE SENSOR BASED ON PHOTOADDRESSABLE POLYMERS

(75) Inventors: Ingmar Dorn, Köln (DE); Thomas Bieringer, Odenthal (DE); Rainer Hagen, Leverkusen (DE); Serguei Kostromine, Swisttal (DE); Rino E. Kunz, Neuchatel (CH)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 10/969,814

(22) Filed: Oct. 20, 2004

(65) Prior Publication Data

US 2005/0094958 A1    May 5, 2005

(30) Foreign Application Priority Data

Oct. 29, 2003    (DE) .............................. 103 50 526

(51) Int. Cl.
*G02B 6/10*    (2006.01)
(52) U.S. Cl. ......................... 385/129; 385/14; 385/15; 385/130
(58) Field of Classification Search .................. 385/14, 385/15, 129–133; 264/1.24–1.29; 216/24; 430/270.1
See application file for complete search history.

(56) References Cited

U.S. PATENT DOCUMENTS

| 6,194,120 B1 | 2/2001 | Chan et al. .............. 430/270.1 |
| 6,603,916 B1 * | 8/2003 | McGreer et al. ............ 385/129 |

FOREIGN PATENT DOCUMENTS

| WO | WO 01/06240 A1 | 1/2001 |
| WO | WO 01/06305 A2 | 1/2001 |

OTHER PUBLICATIONS

Applied Physics Letter, Bd. 66, Nr. 9, Feb. 27, 1995, pp. 1050-1052 "Novel second-order nonlinear optical, aromatic, and aliphatic polymides exhibiting high-temperature stability". XP 002314169.

Sensors And Actuators B, Bd. 50, 1998, pp. 210-219, "Integrated optical pH sensor using replicated chirped grating under coupler sensor chips". XP 002314170.

* cited by examiner

*Primary Examiner*—Phan Palmer
(74) *Attorney, Agent, or Firm*—Norris McLaughlin & Marcus, P.A.

(57) ABSTRACT

An optical layer structure having at least two layers and also a sensor based on this layer structure are described. The layer structure comprises at least a substrate layer and at least one (light) waveguide layer and a coupling element for the coupling of the optical beam, the layer adjacent to the waveguide layer having a smaller refractive index than the waveguide layer, and at least one layer consisting of a photoaddressable polymer.

33 Claims, 2 Drawing Sheets

LAYER STRUCTURE AND OPTICAL WAVEGUIDE SENSOR BASED ON PHOTOADDRESSABLE POLYMERS

The invention relates to optically integrated waveguide sensors based on photoaddressable polymers and to their use as bio- or chemosensors.

Bio- or chemosensors refer to instruments which can qualitatively or quantitatively detect an analyte with the aid of a signal converter and a recognition reaction. A recognition reaction is defined quite generally as the specific binding or reaction of an analyte with a recognition element. Examples of recognition reactions are the binding of ligands to complexes, the complexation of ions, the binding of ligands to (biological) receptors, membrane receptors or ion channels, of antigens or haptens to antibodies, of substrates to enzymes, of DNA or RNA to certain proteins, the hybridization of DNA/RNA/PNA or the processing of substrates by enzymes. Analytes may be: ions, proteins, natural or synthetic antigens or haptens, hormones, cytokines, mono- and oligosaccharides, metabolism products, or other biochemical markers which are used in diagnosis, enzyme substrates, DNA, RNA, PNA, potential active ingredients, medicaments, cells, viruses. Examples of recognition elements are: complexing agents for metals/metal ions, cyclodextrins, crown ethers, antibodies, antibody fragments, anticalins (Beste, G.; Schmidt, F. S.; Stibora, T.; Skerra A.; *Proc. Natl. Acad. Sci. USA* (1999) 96, 1898–1903), enzymes, DNA, RNA, PNA, DNA/RNA-binding proteins, enzymes, receptors, membrane receptors, ion channels, cell adhesion proteins, gangliosides, mono- or oligosaccharides.

These bio- or chemosensors may be used in environmental analysis, the nutrition sector, human and veterinary diagnostics and crop protection in order to determine analytes qualitatively and/or quantitatively. The specificity of the recognition reaction enables even analytes in complex samples, for example atmospheric air, contaminated water or body fluids, to be determined qualitatively or quantitatively only with minor preceding purification, if any. In addition, bio- or chemosensors may also be used in (bio) chemical research and the search for active compounds in order to investigate the interaction between two different substances (for example between proteins, DNA, RNA, or biologically active substances and proteins, DNA, RNA, etc.).

The recognition reaction may be integrated with the signal converter to give a bio- or chemosensor by immobilizing the recognition element or the analyte on the surface of the signal converter. The recognition reaction, i.e. the binding or the reaction of the analyte with the recognition element results in a change in the optical properties of the medium directly on the surface of the signal converter (for example changing the optical refractive index, the absorption, the fluorescence, the phosphorescence, the luminescence, etc.), which is converted by the signal converter to a measurement signal.

Optical waveguides are a class of signal converters by which the change in the optical properties of a medium can be detected, said medium bordering a waveguide layer. When light is transported as a conducted mode in the waveguide layer, the light field does not terminate abruptly at the medium/waveguide interface, but rather decays exponentially in the detection medium adjoining the waveguide. This exponentially decaying light field is referred to as an evanescent field. When the optical properties of the medium bordering the waveguide change (for example change in the optical refractive index (Tiefenthaler et al.; U.S. Pat. No. 4,815,843 (1989)), in the luminescence (Kunz R.; U.S. Pat. No. 5,442,169 (1995)) within the evanescent field, this may be detected using a suitable measurement setup. It is crucial for the use of waveguides as signal converters in bio- or chemosensors that the change in the optical properties of the medium is detected only very close to the surface of the waveguide. This is because immobilization of the recognition element or of the analyte at the interface of the waveguide may result in the binding to the recognition element, or the reaction on the recognition element, being detected in a surface-sensitive manner when the optical properties of the detection medium (liquid, solid, gaseous) change at the interface of the waveguide.

For practical applications, the following requirements are desirable:

simple, inexpensive production (relating in particular to waveguide production by means of "compatible processes" and the fabrication of the necessary macro-, micro- and nanostructures);

high sensitivity of the sensor;

small dimensions of the measurement fields on a biosensor chip;

good stability (short-term (small drift) and long-term (good durability)).

Immunoassays require: max. 10–15 min incubation time and max. 1 min measurement time; DNA measurements require: a temperature up to 95° C., an incubation time up to 16 h; but the measurement takes max. 1 min. The measurements commonly take place predominantly in aqueous media, in which case the pH is, for example, between 5 and 9 and the salt content is up to 1.5 mol/l. The chips should in particular be storable for 2 years (in the dark).

There is always good compatibility for application of recognition molecules in the case of polymer coatings, since, for example, reactive groups can be introduced into the polymer, either as early as in the course of synthesis before the coating or after the coating, either via physisorption or chemisorption. Processes such as plasma treatment of the polymer surface and subsequent physisorption of the biomolecules are also conceivable (for example as in the case of coating of microtitre plates which are first plasma-treated and then coated with proteins.

One approach for fulfilling the requirements is described in the Laid-Open Specification WO 01/06240 A1. However, this application has the following disadvantages:

The sensitivity can only be made sufficiently large by using very long optical paths. Since the refractive index of the proposed material is <1.66, very large measurement distances result, and the requirements regarding sensitivity and dimension cannot be simultaneously fulfilled.

To fulfil the requirements, it is advantageous to use materials for the waveguide production which firstly have a very high refractive index (>1.7) for the waveguide structure (layer or region) and a very low refractive index (<approx. 1.4) for the adjoining layers or regions in which the transversely damped (evanescent) field fractions of the conducted waves propagate.

Since high measurement sensitivity is of central importance, great efforts have been made here in the last few years. Some further examples of approaches to solutions are discussed hereinbelow with reference to publications and patents.

It is conceivable to use high-refractive index inorganic layers on glass.

One example thereof is described in the publication [K. Cottier, M. Wiki, G. Voirin, H. Gao, and R. E. Kunz, "Label-free highly sensitive detection of (small) molecules by wavelength interrogation of integrated optical chips", Sensors & Actuators B, vol 91/1–3 pp 241–251 (2003)]. In section 6, the manufacture is described. In this example, a grating structure was initially generated by lithographic means in a glass substrate, then a tantalum pentoxide layer was applied as a waveguide and the coupling structure was then generated in a further step by means of "localized deep etching". Each of these steps consists of several intermediate steps.

One known waveguide consists of hard dielectric materials.

A technically complicated structuring by means of photolithography is therefore necessary.

This in turn results in a high (production) cost for such waveguides.

It is known that glass can also be structured by pressing, casting and embossing, but these processes are very complicated and difficult to control. Another problem is the wear and ageing of the tools used.

Too many process steps such as photolithography, etching, lifting off, atomizing under reduced pressure, etc. are needed in the prior art and each step additionally introduces contaminations that lead to defects in the waveguide. For example, (small) regions may occur in which the grating (nano)structure is disrupted or is entirely absent, so that localized variation of the grating coupling efficiency then occurs, which leads to measurement errors, especially in the case of small spots on chips for fluorescent sensor technology.

Also occasionally described are high-refractive index inorganic layers on carbon substrates.

Also conceivable are high-refractive index inorganic layers on carbon substrates. Such chips have been described, for example, in the publications [J. Dübendorfer, R. E. Kunz, G. Jobst, I. Moser and G. Urban, "Integrated Optical pH Sensor using Replicated Chirped Grating Coupler sensor Chips", Sensors and Actuators B, Vol. 50/3, 210–219 (1998)] and [L. U. Kempen and R. E. Kunz, "Replicated Mach-Zehnder Interferometers with Focusing Grating Couplers for Sensing Applications", Sensors and Actuators B, Vol. 38–39, 295–299 (1997)].

In the publication of Dübendorfer et al., the sensor chips were produced by initially embossing the grating structure by replication into a polycarbonate substrate (see section 3 of this publication), and then the chip was coated with a titanium dioxide waveguide layer. The grating structures were formed here as chirped gratings having a grating constant varying with location.

The publication of Kempen et al. describes both Mach-Zehnder interferometers and focusing coupling and decoupling structures. Section 3 describes the production. Here, chips were produced by replication in polycarbonate substrates (films) and subsequent coating with an inorganic waveguide layer. In this example, a 260 nm-thick SiNx layer was deposited on the replicated surface relief in polycarbonate by means of a plasma-enhanced chemical-vapour deposition (PECVD) process.

Although the replication of the substrate is inexpensive, the application of the high-refractive index layer in the case of such waveguides is expensive and problematic. The waveguide layer properties are not optimal (disadvantages are: typical strong light scattering, pores, mechanical stresses).

The production process is complicated, especially the deposition processes as such, and additionally the application of adhesion promoters, barrier layers, etc.

Further problems include: the light absorption of the polymer; stresses between the layers owing to different expansion coefficients; the detachment of the layers in the course of chemical pretreatment.

It is an object of the invention to provide a detection platform which circumvents the abovementioned disadvantages, with the waveguides that aresimple to produce, and demonstrate high sensitivity, in the foreground.

The invention relates to optically integrated detection platforms and to a layer structure therefor, which have at least one layer, or more generally one region which consists of a photoaddressable polymer (PAP).

The invention provides an optical layer structure having at least two layers, comprising at least a substrate layer and at least one (light) waveguide layer and a coupling element for the coupling of the optical beam, in particular an optical grating, a prism or a planar or curved transparent top surface of the waveguide layer, the layer adjacent to the waveguide layer having a smaller refractive index than the waveguide layer, characterized in that at least one layer consists of a photoaddressable polymer.

The inventive photoaddressable polymer is preferably polymeric or oligomeric organic material, more preferably a side chain polymer.

The main chains of the side chain polymers stem from the following basic structures: polyacrylate, polymethacrylate, polyacrylamide, polymethacrylamide, polysiloxane, polyurea, polyurethane, polyester, polystyrene or cellulose. Preference is given to polyacrylate, polymethacrylate and polyacrylamide.

The inventive polymers and oligomers preferably have glass transition temperatures $T_g$ of at least 40° C., more preferably of at least 90° C. The glass transition temperature may be determined, for example, according to B. Vollmer, Grundriß der Makromolekularen Chemie [Outline of macromolecular chemistry], p. 406–410, Springer Verlag, Heidelberg 1962.

The inventive polymers and oligomers have a weight-average molecular weight of 5000 to 2 000 000 g/mol, preferably of 8000 to 1 500 000 g/mol, determined by gel-permeation chromatography (calibrated with polystyrene).

According to the invention, the side chains of the photoaddressable polymers which are provided are azo dye fragments and also optionally at least one moiety having shape anisotropy (mesogen).

In the polymers used with preference in accordance with the invention, azo dyes are covalently bonded to the polymer main chain, generally via flexible spacers. The azo dyes interact with the electromagnetic radiation and change their spatial orientation.

The mesogens are generally attached in the same way as the azo dyes. They do not necessarily have to absorb the actinic light because they function as a passive molecular group. They are thus not photoactive in the above sense. It is their task to enhance the light-inducible birefringence and to stabilize it after the action of light.

The realignment of the dyes after the illumination with actinic light results, for example, from investigations of polarized absorption spectroscopy: a sample which has been illuminated beforehand with actinic light is investigated in the spectral region of the absorption of the dyes between two polarizers in a UV/VIS spectrometer (for example from CARY 4G, UV/VIS spectrometer). When the sample is rotated about the sample normals and the polarizer arrangement is suitable, for example in the crossed state, the realignment of the dyes follows from the intensity profile of the extinction as a function of the sample angle and can thus be determined unambiguously.

A parameter that is important is the alignment of the longitudinal molecular axis. The longitudinal molecular axis may be determined, for example, by molecular modelling (e.g. CERIUS$^2$) with reference to the molecular shape.

The moiety which interacts with the electromagnetic radiation is an azo dye. The inventive material consequently comprises at least one azo dye.

Azo dyes have, for example, the following structure of the formula (I)

(I)

where

R$^1$ and R$^2$ are each independently hydrogen or a nonionic substituent and m and n are each independently an integer from 0 to 4, preferably 0 to 2.

X$^1$ and X$^2$ are —X$^{1'}$—R$^3$ or X$^{2'}$—R$^4$ where

X$^{1'}$ and X$^{2'}$ are each a direct bond, —O—, —S—, —(N—R$^5$)—, —C(R$^6$R$^7$)—, 13 (C=O)—, —(CO—O)—, —(CO—NR$^5$)—, —(SO$_2$)—, —(SO$_2$—O)—, —(SO$_2$—NR$^5$)—, —(C=NR$^8$)— or —(CNR$^8$—NR$^5$)—, R$^3$, R$^4$, R$^5$ and R$^8$ are each independently hydrogen, C$_1$- to C$_{20}$-alkyl, C$_3$- to C$_{10}$-cycloalkyl, C$_2$- to C$_{20}$-alkenyl, C$_6$- to C$_{10}$-aryl, C$_1$- to C$_{20}$-alkyl-(C=O)—, C$_3$- to C$_{10}$-cycloalkyl-(C=O)—, C$_2$- to C$_{20}$-alkenyl-(C=O)—, C$_6$- to C$_{10}$-aryl-(C=O)—, C$_1$- to C$_{20}$-alkyl-(SO$_2$)—, C$_3$- to C$_{10}$-cycloalkyl-(SO$_2$)—, C$_2$- to C$_{20}$-alkenyl-(SO$_2$)— or C$_6$- to C$_{10}$-aryl-(SO$_2$)— or X$^{1'}$—R$^3$ and X$^{2'}$—R$^4$ may each be hydrogen, halogen, cyano, nitro, CF$_3$ or CCl$_3$, R$^6$ and R$^7$ are each independently hydrogen, halogen, C$_1$- to C$_{20}$-alkyl, C$_1$- to C$_{20}$-alkoxy, C$_3$- to C$_{10}$-cycloalkyl, C$_2$- to C$_{20}$-alkenyl or C$_6$- to C$_{10}$-aryl.

Nonionic substituents refer to halogen, cyano, nitro, C$_1$- to C$_{20}$-alkyl, C$_1$- to C$_{20}$-alkoxy, phenoxy, C$_3$- to C$_{10}$-cycloalkyl, C$_2$- to C$_{20}$-alkenyl or C$_6$- to C$_{10}$-aryl, C$_1$- to C$_{20}$-alkyl-(C=O)—, C$_6$- to C$_{10}$-aryl-(C=O)—, C$_1$- to C$_{20}$-alkyl-(SO$_2$)—, C$_1$- to C$_{20}$-alkyl-(C=O)—O—, C$_1$- to C$_{20}$-alkyl-(C=O)—NH—, C$_6$- to C$_{10}$-aryl-(C=O)—NH—, C$_1$- to C$_{20}$-alky-O—(C=O)—, C$_1$- to C$_{20}$-alkyl-NH—(C=O)— or C$_6$- to C$_{10}$-aryl-NH—(C=O)—.

The alkyl, cycloalkyl, alkenyl and aryl radicals may in turn be substituted by up to 3 radicals from the group of halogen, cyano, nitro, C$_1$- to C$_{20}$-alkyl, C$_1$- to C$_{20}$-alkoxy, C$_3$- to C$_{10}$-cycloalkyl, C$_2$- to C$_{20}$-alkenyl or C$_6$- to C$_{10}$-aryl, and the alkyl and alkenyl radicals may be straight-chain or branched.

Halogen refers to fluorine, chlorine, bromine and iodine, in particular fluorine and chlorine.

The dyes, in particular the azo dyes of the formula (I) are covalently bonded to the polymer frameworks, generally via a spacer. For example, X$^1$ (or X$^2$) is in that case such a spacer, especially in the definition X$^{1'}$-(Q$^1$)$_i$-T$^1$-S$^1$— where

X$^{1'}$ is as defined above,

Q$^1$ is —O—, —S—, —(N—R$^5$)—, —C(R$^6$R$^7$)—, —(C=O)—, —(CO—O)—, —(CO—NR$^5$)—, —(SO$_2$)—, —(SO$_2$—O)—, —(SO$_2$—NR$^5$)—, —(C=NR$^8$)—, —(CNR$^8$—NR$^5$)—, —(CO—NR$^5$)—, —(CH$_2$)$_p$-, p- or m-C$_6$H$_4$— or a divalent radical of the formulae i is an integer from 0 to 4 and, when i>1, the individual Q$^1$'s may have different definitions, T$^1$ is —(CH$_2$)$_p$— and the chain may be interrupted by —O—, —NR$^9$—, or —OSiR$^{10}$$_2$O—, S$^1$ is a direct bond, —O—, —S— or —NR$^9$—, p is an integer from 2 to 12, preferably 2 to 8, in particular 2 to 4,

R$^9$ is hydrogen, methyl, ethyl or propyl,

R$^{10}$ is methyl or ethyl and

R$^5$ to R$^8$ are each as defined above.

Preferred dye monomers for polyacrylates or polymethacrylates then have the formula (II)

(II)

where

R is hydrogen or methyl and the other radicals are each as defined above.

Particularly suitable dye monomers are of the following formula (IIa)

(IIa)

where

X$^3$ is CN and any other known electron-withdrawing substituents, and R$^1$ is then preferably also CN, and the R, $S^1$, $T^1$, $Q^1$, $X^{1'}$ and $R^2$ radicals, and also i, m and n are each as defined above.

In addition to the dyes, for example of the formula (I), the inventive polymeric or oligomeric organic, amorphous material may bear moieties which are of anisotropic shape. These are also covalently bonded to the polymer skeletons, generally via a spacer.

Moieties of anisotropic shape have, for example, the structure of the formula (III)

(III)

where
Z is a radical of the formulae (IIIa)

(IIIb)

where
A is O, S or N—$C_1$- to —$C_4$-alkyl,
$X^3$ is —$X^{3'}$-$(Q^2)_j$-$T^2$-$S^2$—,
$X^4$ is $X^{4'}$—$R^-$,
$X^{3'}$ and $X^{4'}$ are each independently a direct bond, —O—, —S—, —(N—$R^5$)—, —C($R^6R^7$)—, —(C=O)—, —(CO—O)—, —(CO—$NR^5$)—, —($SO_2$)—, —($SO_2O$)—, —($SO_2$—$NR^5$)—, —(C=$NR^8$)— or —($CNR^8$—$NR^5$)—,
$R^5$, $R^8$ and $R^{13}$ are each independently hydrogen, $C_1$- to $C_{20}$-alkyl, $C_3$- to $C_{10}$-cycloalkyl, $C_2$- to $C_{20}$-alkenyl, $C_6$- to $C_{10}$-aryl, $C_1$- to $C_{20}$-alkyl-(C=O)—, $C_3$- to $C_{10}$-cycloalkyl-(C=O)—, $C_2$- to $C_{20}$-alkenyl-(C=O)—, $C_6$- to $C_{10}$-aryl-(C=O)—, $C_1$- to $C_{20}$-alkyl-($SO_2$)—, $C_3$- to $C_{10}$-cycloalkyl-($SO_2$)—, $C_2$- to $C_{20}$-alkenyl-($SO_2$)— or $C_6$- to $C_{10}$-aryl-($SO_2$)— or
$X^{4'}$-$R^{13}$ may be hydrogen, halogen, cyano, nitro, $CF_3$ or $CCl_3$,
$R^6$ and $R^7$ are each independently hydrogen, halogen, $C_1$- to $C_{20}$-alkyl, $C_1$- to $C_{20}$-alkoxy, $C_3$- to $C_{10}$-cycloalkyl, $C_2$- to $C_{20}$-alkenyl or $C_6$- to $C_{10}$-aryl,
Y is a single bond, —COO—, —OCO—, —CONH—, —NHCO—, —CON($CH_3$)—, —N($CH_3$)CO—, —O—, —NH— or —N($CH_3$)—,
$R^{11}$, $R^{12}$, $R^{15}$ are each independently hydrogen, halogen, cyano, nitro, $C_1$- to $C_{20}$-alkyl, $C_1$- to $C_{20}$-alkoxy, phenoxy, $C_3$- to $C_{10}$-cycloalkyl, $C_2$- to $C_{20}$-alkenyl or $C_6$- to $C_{10}$-aryl, $C_1$- to $C_{20}$-alkyl-(C=O)—, $C_6$- to $C_{10}$-aryl-(C=O)—, $C_1$- to $C_{20}$-alkyl-($SO_2$)—, $C_1$- to $C_{20}$-alkyl-(C=O)—O—, $C_1$- to $C_{20}$-alkyl-(C=O)—NH—, $C_6$- to $C_{10}$-aryl-(C=O)—NH—, $C_1$- to $C_{20}$-alkyl-O—(C=O)—, $C_1$- to $C_{20}$-alkyl-NH—(C=O)— or $C_6$- to $C_{10}$-aryl-NH—(C=O)—, q, r and s are each independently an integer from 0 to 4, preferably 0 to 2, $Q^2$ is —O—, —S—, —(N—$R^5$)—, —C($R^6R^7$)—, —(C=O)—, —(CO—O)—, —(CO—$NR^5$)—, —($SO_2$)—, —($SO_2$—)—, —($SO_2$—$NR^5$)—, —(C=$NR^8$)—, —($CNR^8$—$NR^5$)—, —($CH_2$)$_p$—, p- or m-$C_6H_4$— or a divalent radical of the formulae j is an integer from 0 to 4 and, when j>1, the individual $Q^1$s may have different definitions, $T^2$ is —($CH_2$)$_p$— and the chain may be interrupted by —O—, —$NR^9$—, or —$OSiR^{10}_2$—,

$S^2$ is a direct bond, —O—, —S— or —$NR^9$—, p is an integer from 2 to 12, preferably 2 to 8, in particular 2 to 4, $R^9$ is hydrogen, methyl, ethyl or propyl, and $R^{10}$ is methyl or ethyl.

Preferred monomers having such moieties having shape anisotropy for polyacrylates or polymethacrylates then have the formula (IV)

(IV)

where
R is hydrogen or methyl and
the other radicals are each as defined above.

The alkyl, cycloalkyl, alkenyl and aryl radicals may in turn be substituted by up to 3 radicals from the group of halogen, cyano, nitro, $C_1$- to $C_{20}$-alkyl, $C_1$- to $C_{20}$-alkoxy, $C_3$- to $C_{10}$-cycloalkyl, $C_2$- to $C_{20}$-alkenyl or $C_6$- to $C_{10}$-aryl, and the alkyl and alkenyl radicals may be straight-chain or branched.

Halogen refers to fluorine, chlorine, bromine and iodine, in particular fluorine and chlorine.

Particularly preferred monomers which have shape anisotropy and are of the formula (IV) are, for example:

In addition to these functional monomers, the inventive oligomers or polymers may also comprise monomers which mainly serve to lower the percentage content of functional monomers, especially of dye monomers. In addition to this task, they may also be responsible for other properties of the oligomers or polymers, for example the glass transition temperature, liquid crystallinity, film-forming property, etc.

For polyacrylates or polymethacrylates, such monomers are acrylic or methacrylic esters of the formula (V)

where
R is hydrogen or methyl,
$X^5$ is —O— or —(N—$R^{15}$)—

$R^{14}$ and $R^{15}$ are each independently optionally branched $C_1$- to $C_{20}$-alkyl or a radical containing at least one further acrylic unit, or together form a bridging group —$(CH_2)_f$—, —$CH_2$—$CH_2$—O—$CH_2$—$CH_2$— or —$CH_2$—$CH_2$—N(R)—$CH_2$—$CH_2$— where f is 2 to 6.

However, other comonomers may also be present.

The ratio between II, IV and V is arbitrary. Depending on absorption coefficients of II, the concentration of II is preferably between 0.1 and 100% based on the particular mixture. The ratio between II and IV is between 100:0 and 1:99, preferably between 100:0 and 20:80, most preferably between 100:0 and 50:50.

The structure of the polymers and oligomers allows the intermolecular interactions of the structural elements of the formulae (II) with one another or of the formulae (IV) and (V) with one another to be adjusted in such a way that the formation of liquid-crystalline states of order is suppressed, and optically isotropic, transparent, nonscattering films, foils, plates or cuboids can be produced. Nevertheless, the intermolecular interactions are strong enough that irradiation with light brings about a photochemically induced, cooperative, directed realignment process of the photochromic and the nonphotochromic side groups.

Interactive forces preferably arise between the side groups of the repeating units of the formula (II) or between those of the formula (IV) and are sufficient that the photoinduced change in configuration of the side groups of the formula (II) brings about parallel, known as cooperative, realignment of the other side groups (IV).

In the optically isotropic, amorphous, photochromic polymers, extremely high values of optical anisotropy may be induced (Δn to 0.4).

The influence of actinic light generates states of order in the polymers or oligomers and modifies and thus modulates the optical properties.

The light used is polarized light whose wavelength is in the range of the absorption band, preferably in the range of the long-wavelength n-π* band of the repeating units of the formula (II).

Heat-treatment of the sample aligned with polarized light at temperatures between 70 and 150° C., preferably between 100 and 140° C., allows the optical anisotropy to be increased further.

The preparation of the polymers and oligomers may be carried out by literature processes, for example according to DD 276 297, DE-A 3 808 430, Makromolekulare Chemie 187, 1327–1334 (1984), SU 887 574, Europ. Polym. 18, 561 (1982) and Liq. Cryst. 2, 195 (1987).

Particularly suitable materials contain at least one of the polymers of the formula VI to XI

(VI)

VII

VIII

IX

X

XI

The use of light-sensitive polymers as waveguide material, known as photoaddressable polymers (PAPs), is particularly preferable. The PAPs exhibit very high light-induced changes in refractive index which can be adjusted in a targeted manner via the incident light energy (refractive index n=1.3 to 2.0 and birefringence preferably greater than 0.5 in the VIS spectral region). It is thus possible, in a homogeneous PAP layer, by illumination, to generate regions which have a differing refractive index and can thus be used as optical waveguides or as coupling or decoupling gratings for light, which is not possible with inorganic waveguides. In this way, by illuminating the PAP layer alone, a multitude of separate waveguides can be generated in one layer which are optically divided from each other by the unilluminated regions between them. The same also applies for coupling or decoupling gratings, which allows very simple and flexible production of a multitude of individually addressable sensor regions consisting of coupling grating and waveguide to be produced in one PAP layer. PAP waveguides are thus very suitable for sensor arrays in which several analytes can simultaneously be detected at different wavelengths (multiplexing).

Alternatively, PAP layers which have been applied directly to a waveguide layer may also be used only as coupling or decoupling gratings. The very sensitive light-induced change in refractive index allows absorption or refractive index gratings, also referred to as phase gratings, to be obtained very simply and inexpensively in the PAP layer by iuumination, both within the volume or close to the surface, the surface of the side corresponding to that of the PAP layer which is facing the actinic light. The waves are then guided in the waveguide layer which may consist of organic or inorganic material. This waveguide layer may also be a PAP material which has different optical properties to the PAP layer into which optical gratings have been inscribed.

In addition, some PAP layers exhibit highly marked surface gratings in holographic experiments which occur as a regular profile in the PAP film surface and which can be used as coupling/decoupling gratings for the sensor. They have temperature and long-term stability. The absorption of the PAP materials may be adjusted over a wide wavelength range, so that a high transparency (<3 dB/cm) can be achieved at the laser wavelength used in industry.

The advantages of the PAP layers lie in particular in the light-induced generation of optical waveguide and grating structures. No photolithographic steps and etching steps are needed to generate these structures.

Thin layers (10 nm to 1000 nm) of PAP may be applied to a suitable substrate material by techniques known in principle, for example spin-coating, spraying, knife-coating, dip-coating, etc. These processes are simpler and less expensive in the production than the atomization or vapor deposition of inorganic waveguides on substrates under high vacuum.

Unlike conventional polymers, PAPs have high refractive indices (up to n=2), which makes them very suitable for use in highly sensitive bio- and chemosensors.

Depending on the implementation, these PAP regions have at least one of the following functions:
1. The realization of regions having very high refractive index, for example to achieve highly sensitive (main) waveguides. Inexpensive and "compatible" production of the layers.
2. The inexpensive, uncomplicated realization of nano-, micro- and macrostructures by means of direct illumination of the PAP material without the need for additional process steps.

This function serves for flexible definition of regions on the platform, which serve for coupling and decoupling of light with great efficiency (for example for grating-based sensor technology, and for definition of sensor and reference measurement fields). Furthermore, structures may also be produced for conducting laterally restricted light waves on the platform, for example for realizing interferometer structures.

One advantage of the invention is a drastic reduction in costs and simplification of the production, since only few process steps are needed and the quality of the layers in the production will be high by virtue of the few process steps (for example attachment of recognition layers, etc). It is possible to incorporate, for example, functional groups into the PAP by copolymerization, or absorb proteins by plasma treatment of the surface. Similarly to the case of microtitre plates, light-induced attachment via photochemistry is also possible.

The adjacency of high and low refractive indices is possible, both in the nanometre range (for example inscribed grating nanostructures) and in the micro- and macroscopic region (for example inscription of strip waveguides and definition of sensor fields having dimensions of micrometres to milli- and centimetres).

Preference is given to a layer structure, which is characterized in that the photoaddressable polymer has a refractive index of >1.65, preferably of >1.75.

Preference is also given to a layer structure, which is characterized in that the waveguide layer has a plurality of light-induced, microscopic and/or macroscopic light-guiding substructures. These have a refractive index which differs distinctly from that of the surrounding regions.

Not only the gratings, but also the waveguides may optionally be generated by light induction.

In a preferred embodiment, the substrate layer is optically transparent.

In the context of the invention, optically transparent means that the material has a transparency of min. 90% for radiation of a wavelength in the range from 450 to 900 mm.

In a preferred alternative embodiment, the substrate layer is optically nontransparent, but an additional buffer layer disposed above the substrate layer is optically transparent.

In a preferred embodiment of the layer structure, the coupling element is a grating.

Particular preference is given to the coupling element being a grating which is mounted in the layer that has the photoaddressable polymer.

Preference is further given to a layer structure in which the waveguide layer is based on photoaddressable polymers.

Particular preference is given to a layer structure in which the waveguide layer is based on a material selected from the group of tantalum pentoxide, titanium dioxide, hafnium dioxide, zinc oxide, niobium pentoxide and zirconium oxide, alone or in a mixture, in particular on titanium oxide.

In a particularly preferred variant of the layer structure, a plurality of gratings of different grating constants are present as coupling elements.

In a preferred embodiment of the invention, the refractive index of the waveguide layer is >1.6, more preferably >1.67.

An advantageous structure of the layer structure is one in which the layer thickness of the waveguide layer is less than the wavelength of the radiation which is conducted in the waveguide.

Very particular preference is given to a layer structure, which is characterized in that the waveguide layer can be operated in single-mode operation.

In a further particular embodiment of the layer structure, a decoupling unit is additionally provided for decoupling the optical beam, in particular an optical grating.

In a particularly preferred form of the layer structure, the thickness of the waveguide layer is 30 to 300 nanometres.

A further particularly preferred embodiment of the layer structure is characterized in that an intermediate layer having a lower refractive index than the waveguide layer is provided between waveguide layer and substrate layer.

In a particularly preferred embodiment of this layer structure, the intermediate layer is based on an optically transparent polymer.

Particular preference is likewise given to another embodiment of the layer structure, which is characterized in that a layer composed of photoaddressable polymers comprises the coupling element and an adjoining layer, especially disposed above the layer having the coupling element, is the waveguide layer.

A particularly preferred detection platform consists of a transparent substrate and one or more optically anisotropic layers based on PAP, into which at least one sensor structure consisting of an optical waveguide and at least one optical grating structure have been inscribed via one or more suitable illumination steps, said structures differing from the unilluminated part of the PAP in that they have a different refractive index, and light, coupled via the grating structures, is transported in the waveguide structure, in whose evanescent field, at the interface from the waveguide to a sample in contact with it, the optical properties of the sample such as refractive index, luminescence, absorption, etc. are detected by a suitable detection instrument.

A preferred integrated optical waveguide for use as a bio- or chemosensor consists, for example, of a transparent substrate and an optically anisotropic layer based on PAP, into which at least one sensor structure consisting of an optical waveguide and at least one optical grating structure have been inscribed via one or more suitable illumination steps, said structures differing from the remainder of the PAP in that they have a different refractive index, and light, coupled via the grating structures, is transported in the waveguide structure via total reflection or as a conducted mode.

Also possible with preference is a detection platform consisting of a transparent substrate, onto which a planar optical waveguide and a thin optically anisotropic layer based on PAP have been applied, into which at least one optical grating structure has been inscribed via one or more suitable illumination steps, said structure differing from the remainder of the PAP in that it has a different refractive index, and light is coupled into the adjacent waveguide via the grating structures and is transported therein, and, in the evanescent light field at the interface from the waveguide to a sample in contact with it, the optical properties of the sample such as refractive index, luminescence, absorption, etc. are detected with a suitable detection instrument.

Preference is then also given to an integrated optical waveguide for use as a bio- or chemosensor, consisting of a transparent substrate and an optically anisotropic layer based on PAP, into which at least one sensor structure consisting of an optical waveguide and at least one optical grating structure have been inscribed via one or more suitable illumination steps, said structures differing from the remainder of the PAP in that they have a different refractive index, and light, coupled via the grating structures, is transported in the waveguide structure via total reflection or as a conducted mode.

A preferred detection platform consists, for example, of a transparent substrate and an optically anisotropic layer based on PAP, into which at least one sensor structure consisting of an optical waveguide and at least one optical grating structure has been inscribed via one or more suitable illumination steps, said structures differing from the remainder of the PAP in that they have a different refractive index, and light, coupled via the grating structures, is transported in the waveguide structure whose evanescent field at the interface from the waveguide to a sample in contact therewith excites luminescable substances to luminescence and the luminescence radiated into the space is detected with a suitable detection instrument.

A particularly preferred detection platform consists of a transparent substrate and an optically anisotropic layer based on PAP, into which at least one sensor structure consisting of an optical waveguide structure which lies between two optical grating structures has been inscribed via one or more suitable illumination steps, said structures differing from the remainder of the PAP in that they have a different refractive index, and light, coupled via one of the grating structures, is transported in the waveguide structure, whose evanescent field, at the interface from the waveguide to a sample in contact with it, excites luminescable substances to luminescence, and the light back-coupled into the waveguide is decoupled again at the second grating and is detected with a suitable detection instrument.

It is decisive for the use of waveguides as signal converters in bio- or chemosensors that the change in the optical properties of the medium is detected only very close to the surface of the waveguide. This is because immobilization of the recognition element or of the analyte at the interface of the waveguide allows the binding to the recognition element or the reaction of the recognition element to be detected in a surface-sensitive manner when the optical properties of the detection medium (liquid, solid, gaseous) change at the interface to the waveguide.

Special preference is given to an integrated optical waveguide consisting of a transparent substrate and an optically anisotropic layer based on PAP, into which at least one sensor structure consisting of an optical waveguide and at least one optical grating structure have been inscribed via one or more suitable illumination steps, said structures differing from the remainder of the PAP in that they have a different refractive index, and light, coupled via the grating structures, is transported in the waveguide structure.

The invention further provides a sensor comprising a sensor layer, a light source and a recognition layer, and also an optical detector for luminescence, scattered light, absorption or change in the refractive index, comprising an inventive layer structure.

Bio- or chemosensors refer to instruments which can qualitatively or quantitatively detect an analyte with the aid of a signal converter (sensor layer) and a recognition reaction. A recognition reaction is defined quite generally as the specific binding or reaction of an analyte with a recognition element. Examples of recognition reactions are the binding of ligands to complexes, the complexation of ions, the binding of ligands to (biological) receptors, membrane receptors or ion channels, of antigens or haptens to antibodies, of substrates to enzymes, of DNA or RNA to certain proteins, the hybridization of DNA/RNA/PNA or the processing of substrates by enzymes. Analytes may be: ions, proteins, natural or synthetic antigens or haptens, hormones, cytokines, mono- and oligosaccharides, metabolism products, or other biochemical markers which are used in diagnosis, enzyme substrates, DNA, RNA, PNA, potential active ingredients, medicaments, cells, viruses. Examples of recognition elements are: complexing agents for metals/metal ions, cyclodextrins, crown ethers, antibodies, antibody fragments, anticalins, enzymes, DNA, RNA, PNA, DNA/RNA-binding proteins, enzymes, receptors, membrane receptors, ion channels, cell adhesion proteins, gangliosides, mono- or oligosaccharides.

The recognition reaction may be integrated with the signal converter, for example the inventive layer structure, directly or via an organic intermediate layer to give a bio- or chemosensor by immobilizing the recognition element or the analyte on the surface of the signal converter. The recognition reaction, i.e. the binding or the reaction of the analyte with the recognition element results in a change in the optical properties of the medium directly on the surface of the signal converter (for example changing the optical refractive index, the absorption, the fluorescence, the phosphorescence, the luminescence, etc.), which is converted by the signal converter to a measurement signal.

The invention further provides the use of the aforementioned sensor for analyzing biomolecules, markers and active ingredients in environmental analysis, the nutrition sector, human and veterinary diagnostics, (bio)chemical research and the search for active compounds.

These bio- or chemosensors may be used in environmental analysis, the nutrition sector, human and veterinary diagnostics and crop protection in order to determine analytes qualitatively and/or quantitatively. The specificity of the recognition reaction enables even analytes in complex samples, for example atmospheric air, contaminated water or body fluids to be determined qualitatively or quantitatively only with minor preceding purification, if any. In addition, bio- or chemosensors may also be used in (bio) chemical research and the search for active compounds in order to investigate the interaction between two different substances (for example between proteins, DNA, RNA, or biologically active substances and proteins, DNA, RNA, etc.).

The invention further provides a process for recognizing biomolecules using an inventive sensor.

DESCRIPTION OF THE DRAWINGS

The invention is illustrated in detail by way of example hereinbelow with reference to figures. The figures show:

FIG. 1a–f various embodiments of an inventive layer structure in schematic representation FIG. 2 the sensor sensitivity for a layer structure of FIG. 1(a), i.e. the change in the effective refractive index N for a change in the thickness h1 of a (bio)chemical additional layer (for example by the adsorption of molecules from the analyte medium (refractive index nc=1.33)) which is additionally disposed on the basic layer structure in order, in accordance with the invention, to realize a refractometry sensor chip therefrom. The remaining data are as follows: the substrate 2 consists here of glass having a refractive index ns=1.521; the sensitivity curves are shown for a waveguide layer 1 having refractive indices nf=1.6/1.75/1.95/2.15/2.35 as a function of the film thickness hf. The results are valid for the propagation of a TM0 mode having a wavelength of 633 nm. The figure shows clearly that it is essential to use a layer 1 having a refractive index nf of distinctly more than 1.6. From the figure, the optimum thickness hf of the layer 1 in each case can be read off, and also the maximum achievable sensitivity.

The factor is a measure of the fraction of the fluorescence radiation which is radiated into the waveguide, i.e. a factor 2× larger means that 2× more energy gets into the waveguide. It has been assumed that the molecules are disposed directly on the waveguide. FIG. 3(a) shows the fluorescence coupling factor for the radiation in the TM mode at wavelength 633 nm, while FIG. 3(b) shows the ratios for the radiation in the TE mode. A comparison of Figures (a) and (b) for the example of a layer refractive index nf=1.95 shows that radiation in the TM mode (maximum factor approx. 1 at a layer thickness hf of approx. 180 nm) is about 3× more efficient than radiation in the TE mode (maximum factor approx. 0.3 at a layer thickness of about 90 nm). This example is valid for a region of the waveguide without coupling grating.

EXAMPLES

Figure 1:
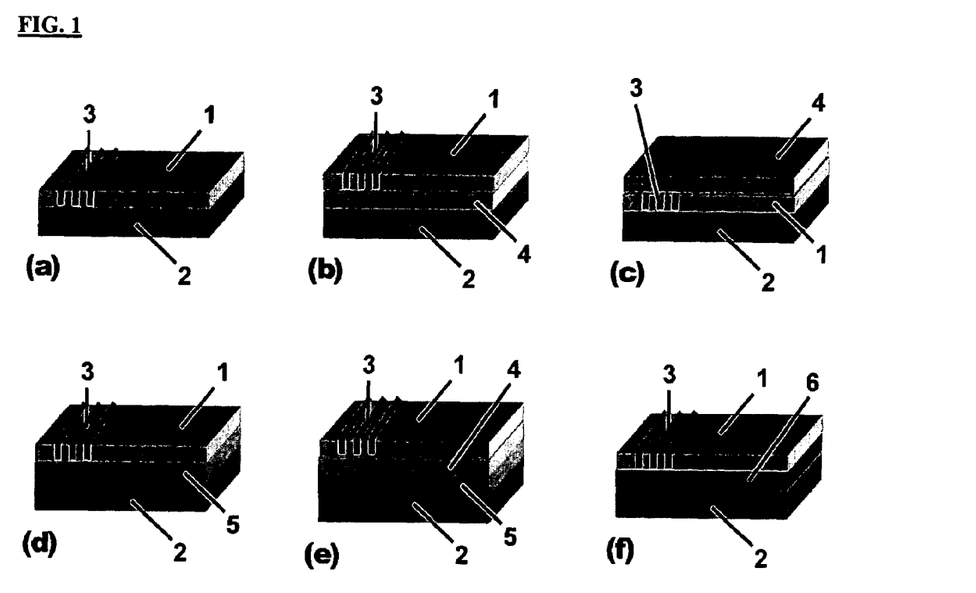
Figure 2:
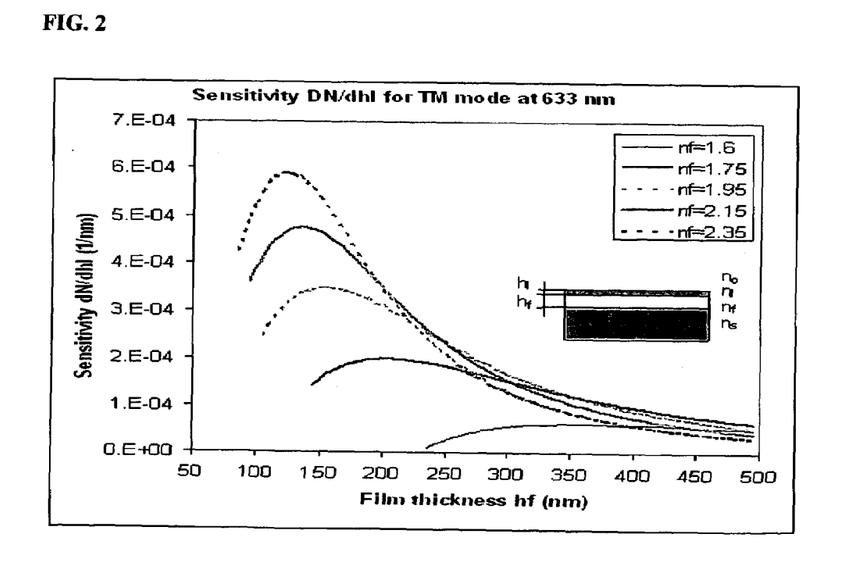
Figure 3:
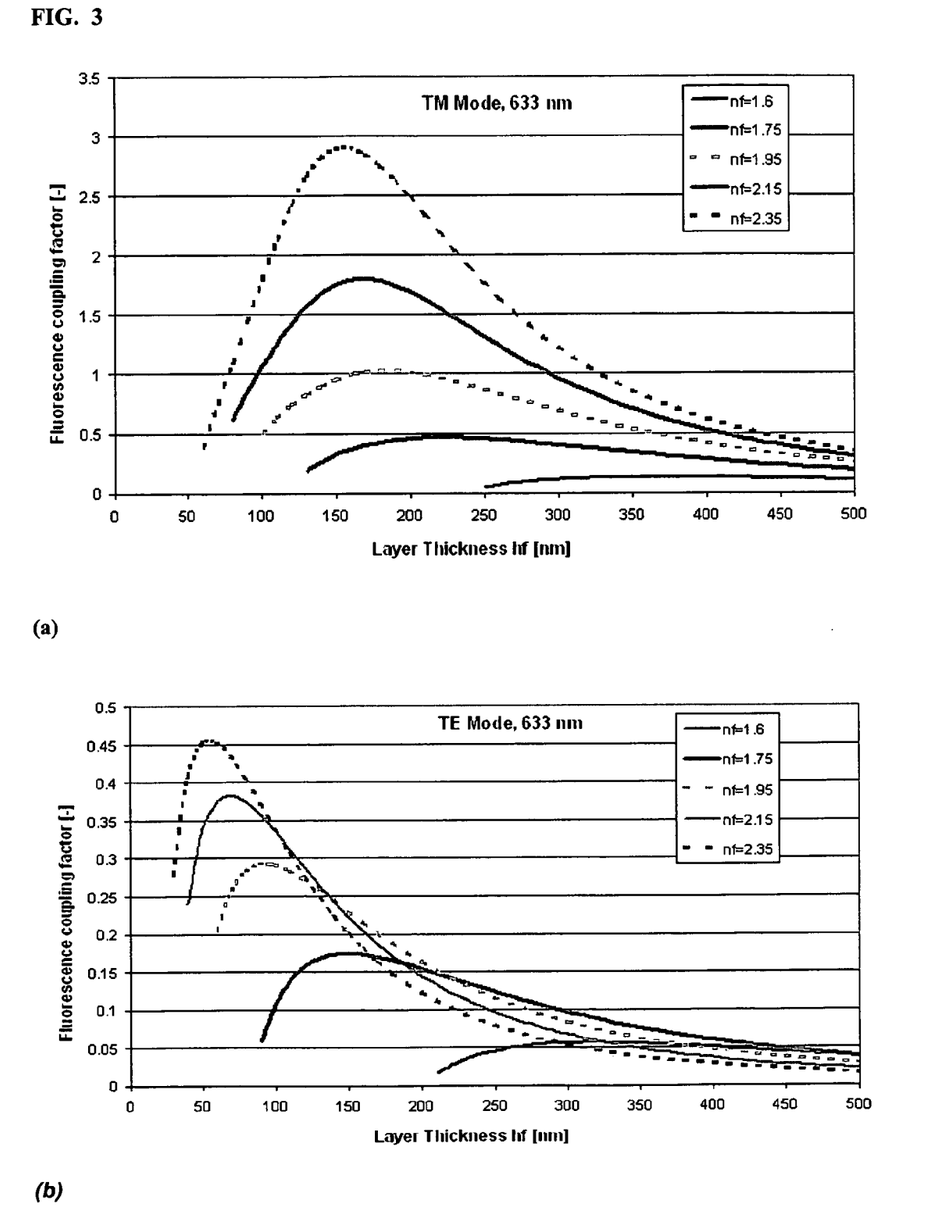
FIG. 3 the coupling factor for fluorescence emission of emitting centres (for example molecules) into the waveguide. The precise definition of the coupling factor is described in the publication [G. Voirin et al., "Si3N4/SiO2/Si waveguide grating for fluorescent biosensors", Proc. SPIE, Vol. 3620 (1999)]. The layer structure data are the same as for FIG. 2, i.e. the same layer structure is used to realize a sensor chip which is used in a fluorescence-based sensor in order to measure the fluorescence emission of centres which are in the vicinity of the waveguide surface.

FIG. 1(a) shows one embodiment of the layer structure in which the PAP layer 1 is simultaneously the waveguide layer and has been applied directly to an optically transparent substrate 2. The layer structure 3 has been produced directly in the layer 1. For the production, only two process steps are needed, i.e. the application of the layer 1 and the illumination of the grating structure 3. Preferred materials for the substrate are plastics and glass.

FIG. 1(b) shows a variant in which a further layer 4 having high refractive index is disposed between the PAP layer 1 and the substrate. Advantages of this variant are that the properties of the layer 1 can be adapted to the optimum inscription of the grating structure 3, while a high-refractive index polymer layer can be used for the waveguide layer 4, whose properties can be optimized with regard to low damping of the modes being propagated therein and/or low scatter. The layer 4 may also be a PAP layer, but does not have to be. The refractive indices of the layers 1 and 4 may be the same or different. However, layer 4 has to have a higher refractive index than the substrate layer 2.

FIG. 1(c) shows a variant in which the sequence of the layers 1 and 4 has been reversed. Substantially, the same applies as was stated for figure (b), but here the layer 1 has to have a higher refractive index than the layer 2. For certain applications, an advantage may result in that the surface properties of the layer 4 can be optimized specifically for the coupling of a biochemical recognition layer, while the layer 1 can be optimized for high refractive index and for the generation of the grating structure 3. Furthermore, it may be advantageous to protect the PAP layer from environmental influences with the coupling structure 3 (the layer 1 is not in contact here with the analyte medium, which is in contact only with the layer 4).

FIG. 1(d) shows a working example in which an optically transparent buffer layer 5 is disposed between the layer 1 and the substrate 2. The PAP layer 1 here is the waveguide layer, while the buffer layer 5 has the function of providing a separation between substrate 2 and layer 1, so that the evanescent wave propagates in the layer 5 below the layer 1 and not in the substrate 2. The advantage of this arrangement may be multiple. For example, the refractive index of the buffer layer selected may be very small, so that the evanescent wave penetrates well into the analyte medium on the analyte side (above the layer 1), and larger regions in the vicinity of the waveguide surface can thus also be defined as sample volume. Such arrangements are also referred to as reverse-symmetry waveguides and have been described by Horvath et al. (see Appl. Phys. Lett., Vol. 81/12, pp. 2166–2168 (16 Sep., 2002). Depending on application and production process, a further advantage may be that the substrate layer does not have to be transparent. For example, semiconductors such as silicon, III–V compounds or optoelectronic polymers may be used and active electrical circuits thus also realized in the substrate, which can be used for evaluating the sensor signals (detectors for optical read-out possibly directly in the substrate). However, it is also possible to use metals or other materials, i.e. the sensor chips may be applied to any objects. In this case, the optical readout of the signals is on the side of the layer 1 or else through holes or transparent regions in the substrate layer 2.

FIG. 1(e) shows a somewhat more complicated variant of (d) in which a layer 4 having high refractive index is used between buffer layer 5 and PAP layer 1. Different embodiments are possible. It is of particular interest to optimize the layer 1 for the production of the coupling structure 3 and the attachment of recognition layers, while the layer 4 can be optimized as a waveguide. The further advantages are the same as for the arrangement of FIG. 1(d); in particular, a nontransparent substrate can be used with the additional advantages associated thereby.

FIG. 1(f) shows a further variant where the waveguide layer used is an inorganic high-refractive index layer 6. Available for selection are many materials, for example from the group of tantalum pentoxide, titanium dioxide, hafnium dioxide, zinc oxide, niobium, pentoxide or zirconium oxide, alone or in a mixture, in particular tantalum pentoxide. This variant has advantages, in particular for achieving highest possible sensitivities, since very high refractive indices are available which may be higher than 2.3. Furthermore, such layers can be produced in very good quality. A further advantage here is that neither the substrate layer 2 nor the layer 6 has to be structurable, which, as mentioned before, causes high costs in conventional layer structures. In the variants shown, the coupling structures 3 can be generated conveniently in the PAP layer 1 lying above without further process steps. Even in this case, only few process steps are needed, i.e. (i) deposition of the layer 6 on the substrate 2, (ii) deposition of the layer 1 and (iii) inscription of the coupling structure 3 by illumination.

It is clear that the foregoing description and exemplified embodiments of the invention are not meant to limit the scope of the claims any way. The described and exemplified embodiments are included for illustrative purposes. It is clear that there may exist modifications of the invention that are within the capability of persons with ordinary skill, and that such modifications may be made without departing from the inventive nature of the optical sensing device described and claimed herein.

What is claimed is:

1. An optical layer structure comprising at least one substrate layer, at least one waveguide layer, and at least one coupling element for the coupling of an optical beam, wherein a layer is positioned adjacent to the waveguide layer and possesses a smaller refractive index than the waveguide layer, and wherein at least one layer of the optical layer structure comprises a photoaddressable polymer.

2. The optical layer structure according to claim 1, wherein the photoaddressable polymer comprises at least one chemically bonded dye of the formula (I)

where
R$^1$ and R$^2$ are each independently hydrogen or a nonionic substituent and
m and n are each independently an integer from 0 to 4,
X$^1$ and X$^2$ are —X$^{1'}$—R$^3$ or —X$^{2'}$—R$^4$
where
X$^{1'}$ and X$^{2'}$ are each a direct bond, —O—, —S—, —(N—R$^5$)—, —C(R$^6$R$^7$)—, —(C═O)—, —(CO—O)—, —(CO—NR$^5$)—, —(SO$_2$)—, —(SO$_2$—O)—, —(SO$_2$—NR$^5$)—, —(C═NR$^8$)— or —(CNR$^8$—NR$^5$)—,
R$^3$, R$^4$, R$^5$ and R$^8$ are each independently hydrogen, C$_1$- to C$_{20}$-alkyl, C$_3$- to C$_{10}$-cycloalkyl, C$_2$- to C$_{20}$-alkenyl, C$_6$- to C$_{10}$-aryl, C$_1$- to C$_{20}$-alkyl-(C═O)—, C$_3$- to C$_{10}$-cycloalkyl-(C═O)—, C$_2$- to C$_{20}$-alkenyl-(C═O)—, C$_6$- to C$_{10}$-aryl-(C═O)—, C$_1$- to C$_{20}$-alkyl-(SO$_2$)—, C$_3$- to C$_{10}$-cycloalkyl-(SO$_2$)—, C$_2$- to C$_{20}$-alkenyl-(SO$_2$)— or C$_6$- to C$_{10}$-aryl-(SO$_2$)—, or
X$^{1'}$—R$^3$ and X$^{2'}$—R$^4$ may each be hydrogen, halogen, cyano, nitro, CF$_3$ or CCl$_3$,
R$^6$ and R$^7$ are each independently hydrogen, halogen, C$_1$- to C$_{20}$-alkyl, C$_1$- to C$_{20}$-alkoxy, C$_3$- to C$_{10}$-cycloalkyl, C$_2$- to C$_{20}$-alkenyl or C$_6$- to C$_{10}$-aryl,
nonionic substituents are selected from the group consisting halogen, cyano, nitro, C$_1$- to C$_{20}$-alkyl, C$_1$- to C$_{20}$-alkoxy, phenoxy, C$_3$- to C$_{10}$-cycloalkyl, C$_2$- to C$_{20}$-alkenyl or C$_6$- to C$_{10}$-aryl, C$_1$- to C$_{20}$-alkyl-(C═O)—, C$_6$- to C$_{10}$-aryl-(C═O)—, C$_1$- to C$_{20}$-alkyl-(SO$_2$)—, C$_1$- to C$_{20}$-alkyl-(C═O)—O—, C$_1$- to C$_{20}$-alkyl-(C═O)—NH—, C$_6$- to C$_{10}$-aryl-(C═O)—NH—, C$_1$- to C$_{20}$-alkyl-O—(C═O)—, C$_1$- to C$_{20}$-alkyl-NH—(C═O)— or C$_6$- to C$_{10}$-aryl-NH—(C═O)—,
wherein the alkyl, cycloalkyl, alkenyl and aryl radicals may in turn be substituted up to 3 times by substituents selected from the group consisting of halogen, cyano, nitro, C$_1$- to C$_{20}$-alkyl, C$_1$- to C$_{20}$-alkoxy, C$_3$- to C$_{10}$-cycloalkyl, C$_2$- to C$_{20}$-alkenyl, and C$_6$- to C$_{10}$-aryl, and the alkyl and alkenyl radicals may be straight-chain or branched,
wherein the halogen is selected from the group consisting of fluorine, chlorine, bromine and iodine,
wherein the one or more dyes of the formula (I) are covalently bonded to the polymer framework optionally via at least one spacer having the structure X$^{1'}$-(Q$^1$)$_i$- T$^1$-S$^1$ or X$^{2'}$-(Q$^1$)$_i$—T$^1$—S$^1$, respectively,
where
Q$^1$ is —O—, —S—, —(N—R$^5$)—, —C(R$^6$R$^7$)—, —(C═O)—, —(CO—O)—, —(CO—NR$^5$)—, —(SO$_2$)—, —(SO$_2$—O)—, —(SO$_2$—NR$^5$)—, —(C═NR$^8$)—, —(CNR$^8$—NR$^5$)—, —(CH$_2$)$_p$—, p- or m-C$_6$H$_4$— or a divalent radical of the formulae i is an integer from 0 to 4 and, when i>1, the individual Q$^1$'s may have different definitions,
T$^1$ is —(CH$_2$)$_p$— and the chain may be interrupted by —O—, —NR$^9$—, or —OSiR$^{10}$$_2$O—,
S$^1$ is a direct bond, —O—, —S— or —NR$^9$—,
p is an integer from 2 to 12,
R$^9$ is hydrogen, methyl, ethyl or propyl,
R$^{10}$ is methyl or ethyl,
R$^5$ to R$^8$ are each as defined above and
X$^1$, and X$^2$, are each as defined above.

3. The optical layer structure according to claim 2 wherein the dye of formula I is an azo dye.

4. The optical layer structure according to claim 2, wherein the photoaddressable polymer comprises formula (I), and wherein m and n are integers from 0 to 2.

5. The optical layer structure according to claim 2, wherein the halogen is either fluorine or chlorine.

6. The optical layer structure of claim 2, wherein p is 2 to 8.

7. The optical layer structure of claim 2, wherein p is 2 to 4.

8. The optical layer structure according to claim 1, wherein the photoaddressable polymer is a polymeric or oligomeric organic material.

9. The optical layer structure according to claim 8, wherein the photoaddressable polymer has a refractive index of >1.65.

10. The optical layer structure according to claim 9, wherein the photoaddressable polymer has a refractive index of >1.75.

11. The optical layer structure according to claim 8, wherein the photoaddressable polymer is a side chain polymer.

12. The optical layer structure according to claim 1, wherein the refractive index of the waveguide layer is >1.6.

13. The optical layer structure according to claim 12, wherein the refractive index of the waveguide is >1.67.

14. The optical layer structure according to claim 1, further comprising a decoupling unit.

15. The optical layer structure according to claim 14, wherein the decoupling unit decouples an optical grating.

16. The optical layer structure according to claim 1, further comprising an intermediate layer having a lower refractive index than the waveguide layer, and positioned between the waveguide layer and the substrate layer.

17. The optical layer structure according to claim 16, wherein the intermediate layer comprises an optically transparent polymer.

18. The optical layer structure according to claim 1, wherein the waveguide comprises at least one material selected from the group consisting of tantalum pentoxide, titanium dioxide, hafnium dioxide, zinc oxide, niobium pentoxide and zirconium oxide.

19. The optical layer structure according to claim 1, wherein the waveguide layer comprises titanium oxide.

20. The optical layer structure according to claim 1, wherein the at least one coupling element comprises a plurality of gratings of different grating constants.

21. The optical layer structure according to claim 1, wherein the substrate layer is optically transparent.

22. The optical layer structure according to claim 1, wherein the substrate layer is optically nontransparent, but an additional optically transparent buffer layer is disposed above the nontransparent substrate layer.

23. The optical layer structure according to claim 1, wherein the thickness of the waveguide layer is less than the wavelength of a guided beam of radiation.

24. The optical layer structure according to claim 1, wherein the waveguide layer can be operated in single-mode operation.

25. The optical layer structure according to claim 1, wherein the at least one coupling element is a grating.

26. The optical layer structure according to claim 1, wherein the at least one coupling element is a grating that is mounted in a layer comprising the photoaddressable polymer.

27. The optical layer structure according to claim 1, wherein the thickness of the waveguide layer is 30 to 300 nanometers.

28. The optical layer structure according to claim 1, wherein the waveguide layer comprises the photoaddressable polymer.

29. The optical layer structure according to claim 1, wherein the waveguide layer has a plurality of microscopic and/or macroscopic light-guiding substructures.

30. The optical layer structure according to claim 1, wherein the coupling element comprises a layer of photoaddressable polymers, and further wherein the waveguide layer is positioned above the layer of photoaddressable polymers, and is adjoined thereto.

31. The optical layer structure according to claim 1, further comprising a sensor, wherein the sensor comprises a sensor layer, a light source, a recognition layer, and an optical detector for luminescence, scattered light, absorption or change in the refractive index.

32. The optical layer structure according to claim 1, wherein the coupling element is selected from the group consisting of an optical grating, a prism, a planar transparent top surface of the waveguide layer, and a curved transparent top surface of the waveguide layer.

33. A method of analysis using the optical layer structure according to claim 1 comprising:
   (a) providing a sample comprising one or more molecules to be detected;
   (b) contacting an optical signal-inducing amount of the sample with the sensor to produce an optical signal; and
   (c) measuring the magnitude of the optical signal.

* * * * *